(12) United States Patent
Fehlbaum et al.

(10) Patent No.: US 7,909,828 B2
(45) Date of Patent: Mar. 22, 2011

(54) CONTOURED REAMER TEETH AND METHOD OF MANUFACTURE

(75) Inventors: Philippe Fehlbaum, Lignieres (CH); Andre Lechot, Orvin (CH)

(73) Assignee: Greatbatch Medical S.A., Orvin (CH)

(*) Notice: Subject to any disclaimer, the term of this patent is extended or adjusted under 35 U.S.C. 154(b) by 1209 days.

(21) Appl. No.: 11/257,417

(22) Filed: Oct. 24, 2005

(65) Prior Publication Data

US 2006/0095041 A1   May 4, 2006

Related U.S. Application Data (63) Continuation-in-part of application No. 10/500,944, filed on Jul. 7, 2004, now Pat. No. 7,850,691, and a continuation-in-part of application No. PCT/IB03/00092, filed on Jan. 16, 2003.

(51) Int. Cl.
*A61B 17/70* (2006.01)
(52) U.S. Cl. .................................. 606/81; 606/86 R
(58) Field of Classification Search ............... 606/79–85, 606/89, 91, 170, 176–180; 30/49, 352, 356; 83/468.8, 468.93, 853; 407/53–56, 58–59, 407/61–63

See application file for complete search history.

(56) References Cited

U.S. PATENT DOCUMENTS

| | | | |
|---|---|---|---|
| 499,619 A * | 6/1893 | Weed .............................. 407/29.1 |
| 1,768,463 A * | 6/1930 | Dixon et al. ..................... 241/95 |
| 3,389,447 A * | 6/1968 | Theobald et al. ............ 407/29.1 |
| 4,023,572 A | 5/1977 | Weigand et al. |
| 4,598,447 A * | 7/1986 | Whyde ......................... 168/48.1 |
| 5,116,165 A | 5/1992 | Salyer |
| 5,171,313 A * | 12/1992 | Salyer ........................ 606/86 R |
| 5,222,956 A | 6/1993 | Waldron |
| 5,282,804 A * | 2/1994 | Salyer ........................ 606/86 R |
| 5,299,893 A | 4/1994 | Salyer et al. |
| 5,501,686 A * | 3/1996 | Salyer ............................. 606/79 |
| 5,709,688 A * | 1/1998 | Salyer ............................. 606/81 |
| 5,897,558 A | 4/1999 | Frieze et al. |
| 5,968,049 A * | 10/1999 | Da Rold .......................... 606/80 |
| 6,001,105 A * | 12/1999 | Salyer ............................. 606/81 |
| 6,283,971 B1 * | 9/2001 | Temeles ......................... 606/81 |
| 6,428,543 B1 * | 8/2002 | Salyer ............................. 606/81 |
| D468,398 S * | 1/2003 | Ziemann ..................... D23/238 |
| 6,730,094 B2 * | 5/2004 | Salyer et al. .................... 606/80 |
| 7,217,272 B2 * | 5/2007 | Salyer ............................. 606/80 |
| 7,220,264 B1 * | 5/2007 | Hershberger ................... 606/81 |
| 2003/0220647 A1 * | 11/2003 | McCallum et al. ............. 606/81 |

(Continued)

FOREIGN PATENT DOCUMENTS

DE     1566114     10/1970

(Continued)

*Primary Examiner* — Thomas C Barrett
*Assistant Examiner* — Larry E Waggle, Jr.
(74) *Attorney, Agent, or Firm* — Michael F. Scalise (57) ABSTRACT

An acetabular reamer (10') for cutting a required cut shape. The reamer has a cutting shell (12') having a series of doubly curved cutting teeth (16') thereon of a quantity to substantially reduce a cutting pressure on each tooth as well as to reduce a size of a typical chip generated upon cutting. Substantially all the teeth each have a matched arc cutting edge (20') of substantial length that has a cutting profile which substantially matches a profile of a shape to be cut. The apertures in which the cutting edges are formed has at least one flat edge by which a punch, used in the process of forming the edge may be oriented. Such a configuration reduces the number of teeth required to cut the shape.

11 Claims, 13 Drawing Sheets

U.S. PATENT DOCUMENTS

2005/0059974 A1* 3/2005 Wolford et al. .................. 606/80
2005/0228390 A1* 10/2005 Cutshall et al. .................. 606/81

FOREIGN PATENT DOCUMENTS

| | | |
|---|---|---|
| DE | 3934610 | 4/1991 |
| EP | 0893097 | 1/1999 |
| EP | 0947170 | 10/1999 |
| FR | 1031888 | 6/1953 |
| FR | 2233972 | 1/1975 |
| WO | WO 02/49516 | 6/2002 |
| WO | WO 02/49517 | 6/2002 |
| WO | WO 03/059178 | 7/2003 |

* cited by examiner

CONTOURED REAMER TEETH AND METHOD OF MANUFACTURE

CROSS REFERENCE TO RELATED APPLICATIONS

This application is a continuation-in-part application of U.S. application Ser. No. 10/500,944 filed Jul. 7, 2004, now U.S. Pat. No. 7,850,691 and PCT/IB03/00092 filed Jan. 16, 2003, of the same name, to André LECHOT, the content of which is incorporated herein by reference thereto.

BACKGROUND OF THE INVENTION

The invention relates to surgical products, and in particular, to surgical reamers for cutting shaped cavities in bone.

In order to produce a shaped cavity in bone for a hip implant, which requires smooth walls and accurate shape, it is advantageous that the reamer shell or cutting bowl be hemispherical. Further, the cutting teeth must be properly located and oriented. Still further, the tooth height is important to the size of bone chip and thus to the accuracy of the shape cut by the reamer.

In most cases, an implant in a hip socket is best fixed to a concave, hemispherical cavity. However, such a shape is not strictly necessary. Other acetabular cutting shells are non-hemispherical but the principle explained here may be adapted to include such other geometries.

It is increasingly important, especially with cementless hip surgery, that the acetabulum be reamed to an exact form, generally a hemisphere, thus allowing maximal contact between the bone and the definitive (hemispherical) implant.

Further, there is increasing emphasis on cutting a smaller incision to minimize the trauma to the patient and to aid the rate of recovery. Meeting this additional requirement provides an additional challenge to the designers of medical instruments and implants. In addition, the change in surgical procedure includes the fact that the surgeon now more often maintains the acetabular reamer handle on a single axis rather than performing the step of "sweeping" the end of the tool handle through an angle and thus continuously changing the axis of the reamer cut. If a test is made maintaining a prior art reamer handle on a constant axis, then a series of concentric rings are cut that, on a macro-scale, approximate a hemisphere. When the surgeon "sweeps" the axis of the reamer handle, these irregularities are removed (in a similar manner to polishing) yielding a hemispherical surface.

In an effort to maximize the number of concentric rings, to minimize chatter/vibration and thus approach a smooth hemispherical surface without sweeping, it is desirable to add more teeth. However, when this is done, mechanical strength decreases. Further, for example, with the convention "cheese-grater"-type reamer, as described in U.S. Pat. No. 4,023,572 to Weigand, it is more difficult to insure that the cut profile of each tooth overlaps or that the teeth are properly located with respect to the cutting direction. Larger teeth of conventional form have been attempted but either the chip size and cutting stresses were too large or the reamer was too complex. Further, due to the large opening adjacent the larger teeth, mechanical strength was sacrificed, at least to some degree.

U.S. Pat. No. 5,116,165 to Sayler describes a scraper-type reamer having a limited number of discrete blade-like teeth. These teeth are defined by a single curve of the profile of the form to be cut. In other words, these teeth are flat. Such a tooth form thus is not supported in that no structure is provided to help maintain the form of the tooth (other than the tooth itself) when faced with the sometimes unusually high cutting stresses associated with reaming. Further, the integrity of the spherical form of the reamer can be affected when there are a limited number of extensive slits or cuts in the spherical body of the reamer. This integrity is affected by the fact that high stresses are induced at the relatively sharp corners of the slits.

U.S. Pat. No. 6,730,094 to Sayler describes another embodiment of a scraper-type reamer also having a limited number of discrete blade-like teeth. These teeth too are flat. Such a tooth form is not supported in that no structure is provided to help maintain the form of the tooth (other than the tooth itself) when faced with the sometimes unusually high cutting stresses associated with reaming. Further, the form of the openings provides undesirable snag and tear points (relief slots 40) at the outer edges of the blades, at the point where the supporting portion behind the blades transitions to the shell. During use, these points may inadvertently tear or snag soft tissue against which it slides during use. This is the case too for FIG. 9 of Salyer, presenting the embodiment most likely the most prone to snags and tears (the slot 40 is apparently hidden from view by the tooth).

Often the form of a tooth on a reamer is a function of the original material form, the sheet material, the base diameter of the hemisphere or of the manufacturing method. Often no consideration is given to the form of the cut surface. Therefore, the cut of a single tooth often only approximates the required form of a sphere or a hemisphere. For example, it may yield a planar surface or have a radius different than that required and further generate an overall hemispherical form that is irregular.

Therefore, what is needed is a reamer that minimizes the discrete cut surfaces and generates a series of cuts that comprise a single defined geometry. Further, what is needed is a mechanism for properly locating and orienting the cutting teeth. Still further, what is needed is a tooth form that can be controlled independently of the form of the original material form.

SUMMARY OF THE INVENTION

The above problems are solved through the provision of an acetabular reamer for cutting a required cut shape, the reamer having a cutting shell on which are located a series of doubly-curved cutting teeth thereon of a quantity to substantially reduce a cutting pressure on each tooth as well as to reduce a size of a typical chip generated upon cutting. Substantially all the teeth each have a matched arc cutting edge of substantial length, these cutting edges having a cutting profile which substantially matches a profile of a shape to be cut.

In an advantage, the configuration of the invention reduces the number of teeth required to cut the shape, by approximately 30%, as compared to a standard "cheese-grater"-type reamer. In another advantage, the apertures on which the cutting edge is formed are non-circular, thus providing an indexing surface permitting the accurate locating of tools which form the cutting edge. Still further, by punching up or forming a larger number of smaller teeth, as compared to the scraper-type reamer of the prior art, it is easier to maintain the spherical shape of the reamer.

In still another advantage, the invention thus gives an improved quality and orientation of the cutting edge which results in an improved cut surface while employing fewer teeth.

DETAILED DESCRIPTION OF THE PREFERRED EMBODIMENT

Figure 1:
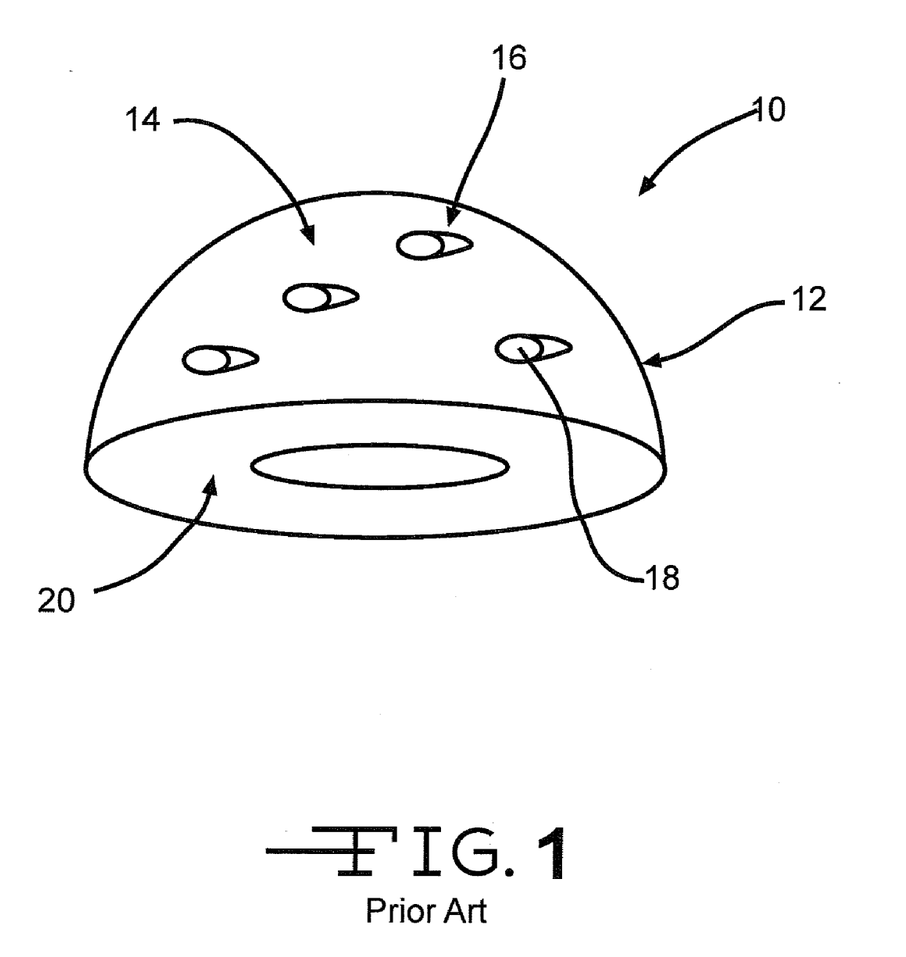
FIG. 1 is a perspective view of a reamer of the prior art.

Referring to FIG. 1, a typical acetabular reamer 10 of the prior art is shown. The reamer 10 has a cutting bowl or shell 12 defining a surface 14 on which are located teeth 16 adjacent openings 18. A base 20 provides a tool-engaging device (not shown).

Figure 2A:
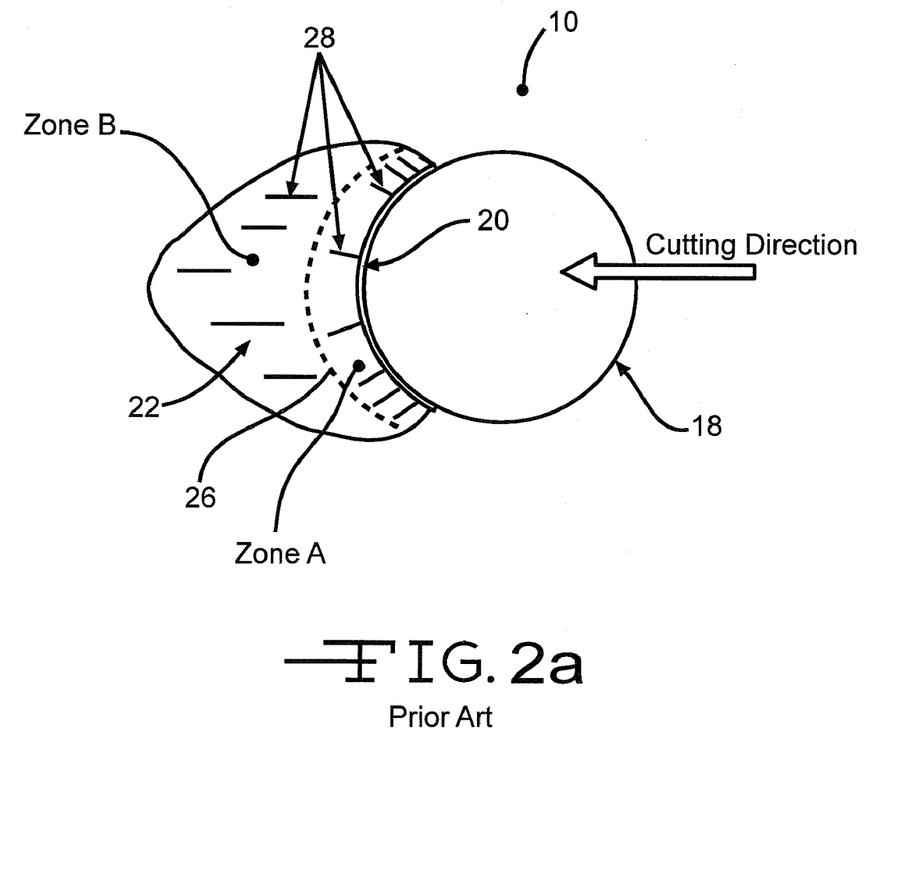
FIG. 2*a* is a top view of a tooth of a reamer of the prior art.

Referring now to FIG. 2a, a tooth 16 of the prior art reamer 10 is shown. The tooth 16 has a diverging surface 22 ("rise", marked Zone A) backing up the cutting edge 20. Some distance behind the cutting edge 20 (to the left of the cutting edge in the figure), about where the dashed line 26 is located, this diverging surface 22 begins to curve inwardly toward the surface of Zone B, and then towards the reamer cutting bowl surface 14 (FIG. 1). Surface reflection lines 28 help indicate the form of these surfaces.

Figure 2B:
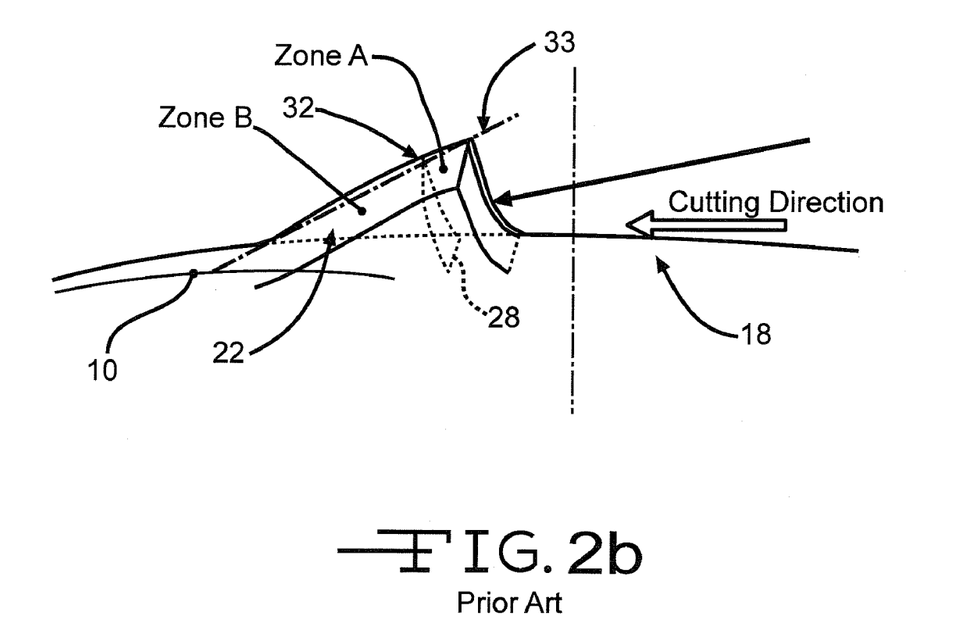
FIG. 2b is a side cross-sectional view of a tooth of a reamer of the prior art.

Referring now to FIG. 2b, a cross sectional side view of the tooth profile 32 of the prior art reamer 10 is shown. The form of the profile 32 of the rise 22 is non-linear as indicated with respect to line 33.

Figure 2C:
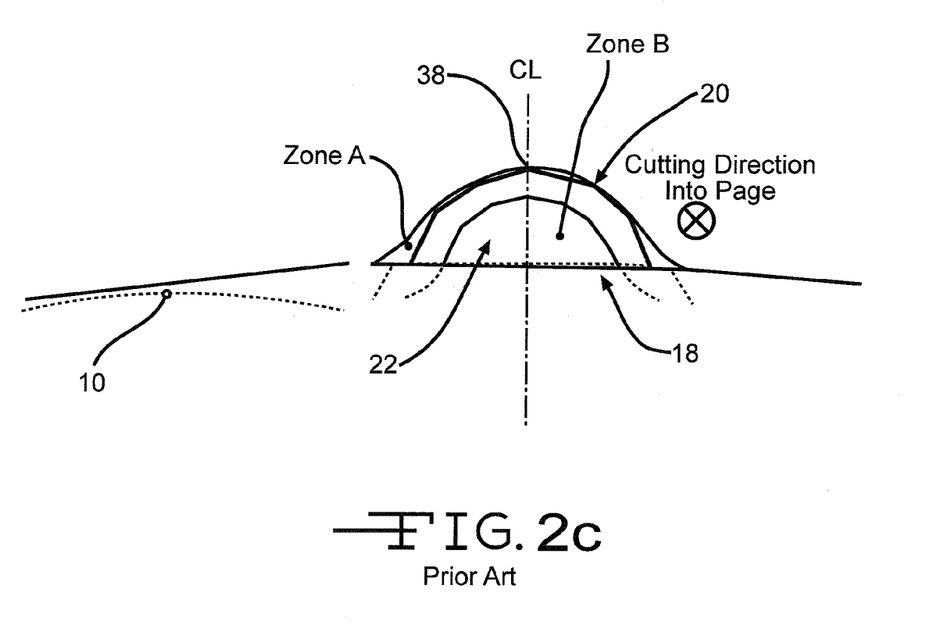
FIG. 2c is a front view of a tooth of a reamer of the prior art.

Referring to FIG. 2c, the diverging surfaces 22 of Zone A are visible when one examines a front view of the tooth 16 of the prior art reamer 10. In other prior art reamers, not shown, corresponding portions of the rise 22 are not visible in a front view but are hidden from view, due to their convergence toward an apex.

These rises 22, respective cutting edges 20, and openings 18 are either positioned on the reamer cutting surface in a spiral arrangement, staggered in another manner, or randomly placed. The term "spiral" is meant to include any form in which the cutting teeth 16 are orderly organized in a manner to sweep out the entire shape to be cut A preferred spiral arrangement is an arrangement in which adjacent teeth are uniformly angularly offset from each other at any adjacent circle of latitude, namely, that adjacent teeth lie on differing circles of longitude evenly spaced apart from one another. Further, it is preferred that there be a given overlap between adjacent cutting rings (i.e., the rings swept out by each tooth 16).

These prior art reamers 10 have a crest 38, which generally approximates a narrow Peak.

Figure 3:
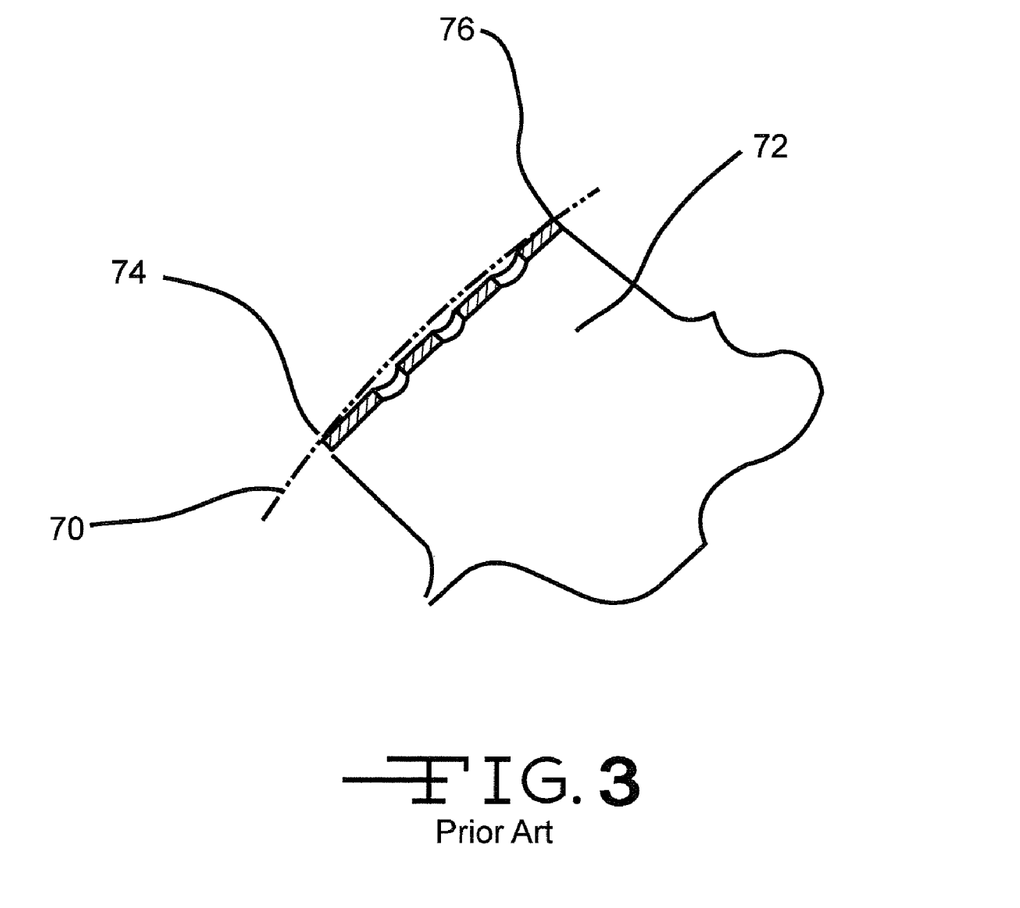
FIG. 3 is a detail view of an alternate tooth of the prior art.

Referring now to FIG. 3, the profile 70 is shown of a prior art tooth 72 of a reamer known as the "DR reamer", the subject of U.S. Pat. No. 5,968,049, the content of which is incorporated herein by reference thereto. The tooth 72 of the DR reamer forms a chord which intersects the profile 70 of the desired cut at two points 74 and 76. Therefore, these prior art reamers have no peak in the typical case.

Figure 4A:
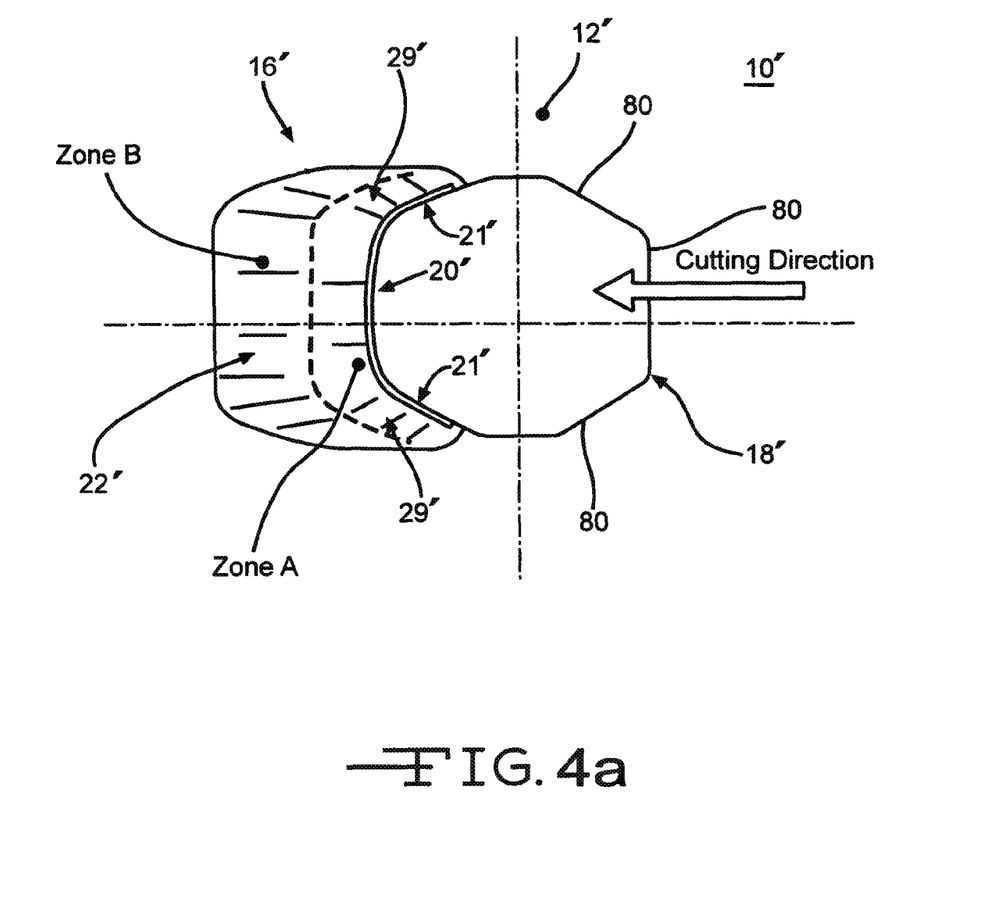
FIG. 4a is a top view of a tooth of a reamer of the prior art.
Figure 4B:
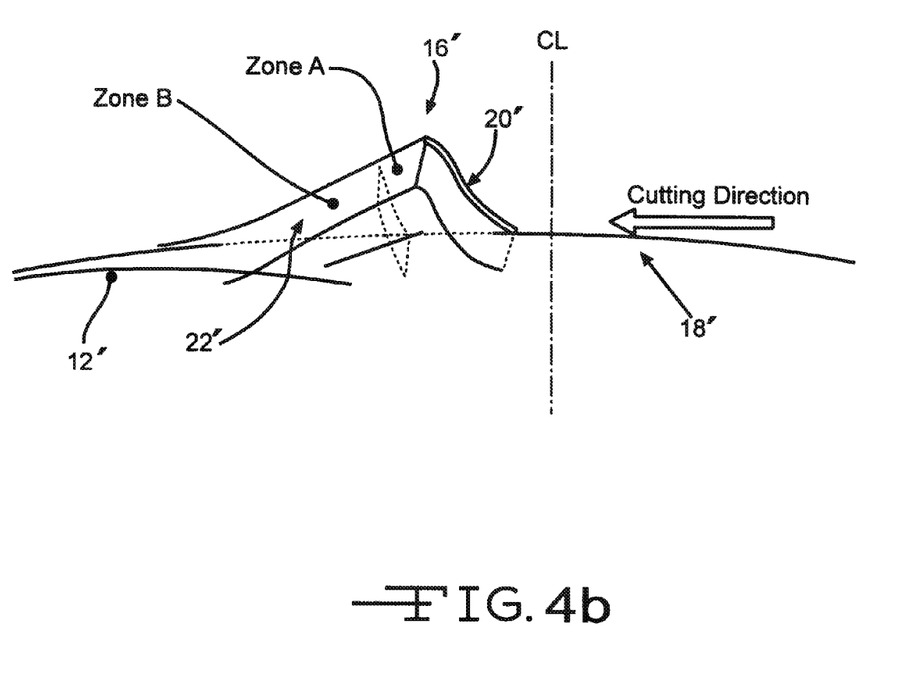
FIG. 4b is a side cross-sectional view of a tooth of a reamer of the prior art.
Figure 4C:
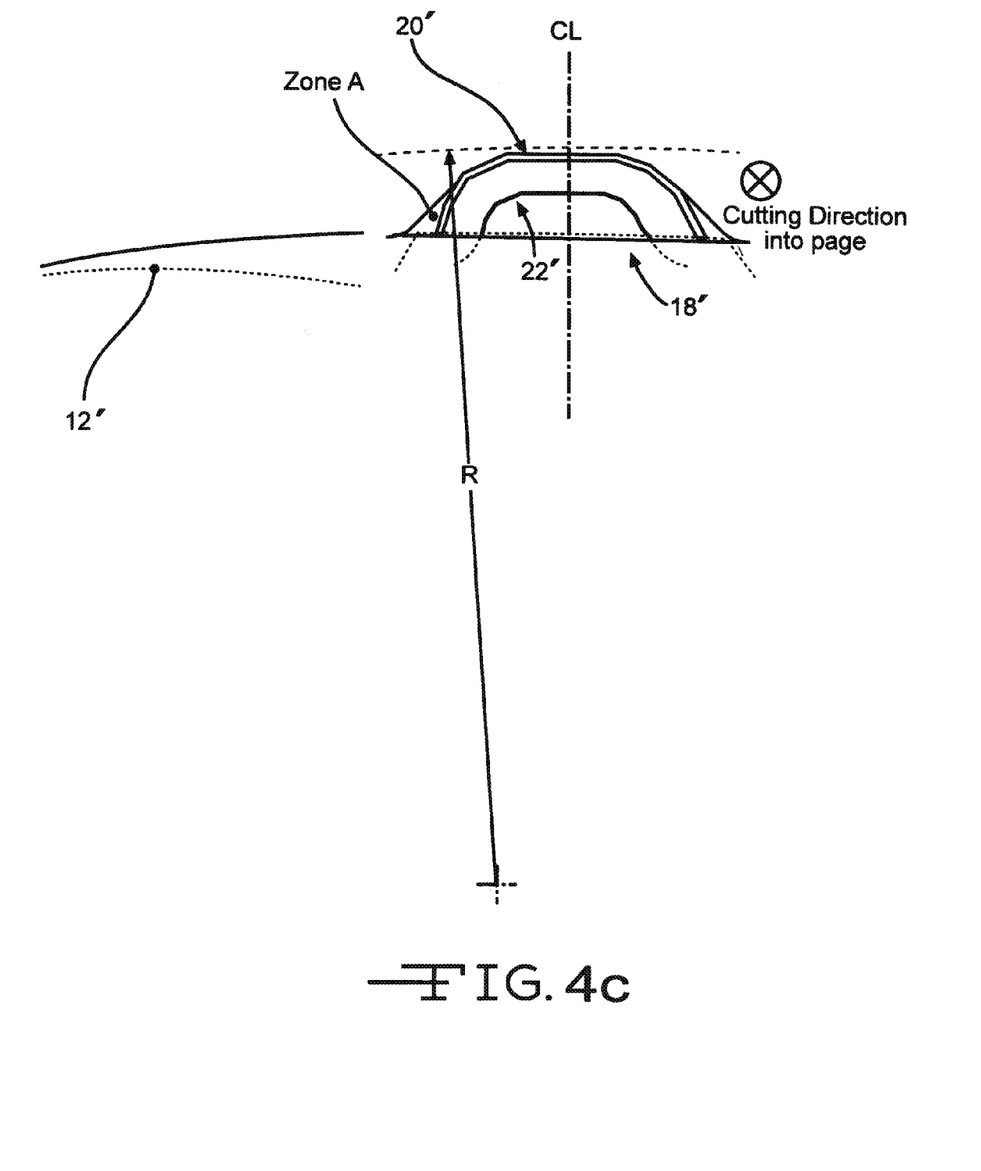
FIG. 4c is a front view of a tooth of a reamer of the prior art.

Referring now to FIGS. 4a to 4c, the present invention has a cutting shell 12' on which are located a series of doubly-curved cutting teeth 16' thereon of a quantity to substantially reduce a cutting pressure on each tooth as well as to reduce a size of a typical chip generated upon cutting. Substantially all the teeth 16' each have a matched arc cutting edge 20' of substantial length that has a cutting profile which substantially matches a profile of a shape to be cut. The matched arc cutting edge 20' is adjacent secondary cutting edges 21' supported by adjacent rise portions 29', characterizable as gusset or buttress portions, which curve back toward the cutting shell 12' and support the secondary cutting edges 21'. The overall cutting edges 20' are therefore doubly-curved in that at least two distinct curves are required to define each cutting edge 20'. A smooth-edged opening 18' precedes the cutting edges as the reamer 10' is rotated for cutting. By defining the openings 18' as being "smooth-edged", it is meant to define a non-circular opening in which there are no slits or narrow grooves which can cause stress concentrations or soft tissue snag or tear points. Such a configuration reduces the number of teeth required to cut the shape and minimizes the risk of snagging or tearing soft tissue during use. The invention thus gives an improved quality of cut surface and allows fewer teeth 16' to be employed.

Although the cutting edge 20' appears flat in the figure, it actually follows the contour of the surface to be cut, in this case, a hemispherical surface. In this embodiment, the radius R of the cutting edge 20' matches the radius of the surface to be cut. Contrary to conventional wisdom, the new tooth 16' is not generated by the manufacture of a larger or wider opening 18 adjacent to the tooth. The opening 18' is, as in the prior art, substantially round in shape. The tooth 16' is generated by the manner in which the tooth is deformed and the profile of the eventual shape. In this embodiment, the rise 22' approximates the shape of a rectangular prism intersecting the cutting bowl at a tangent to the surface of the cutting bowl 12. The teeth 16' have clearly diverging surfaces (in Zone A) which follow the cutting edge 20'. Note that common reference numerals are used for the same or analogous features throughout the drawings.

Further, it has been learned that by forming or punching up more low profile teeth, it is easier to maintain ensure that the spherical shape of the reamer is not compromised.

For any given radius from the center of the acetabulum to the periphery, a different part of the sector is cut by a different tooth 16'. The invention of a longer tooth 16' following the rounded opening 18' and which matches more closely the required radius R, means that a reduced number of teeth are required to cut the full radius. Further, it is believed that although the cutting edge protrudes only 0.5 mm above the surface 14 of the hemispherical shell 12, the fact that the openings are larger means that the effective cutting height may be greater than the 0.5 mm, due to the fact that the perpendicular distance from the center of the outermost edge of the cutting edge 20' and a cord extending across the aperture 18' is significantly greater than 0.5 mm. Further, the use of a series of cutting teeth 16' on the cutting shell 12' substantially reduces the cutting pressure on each tooth as well as reduces the size of a typical chip generated upon cutting. The ability to use fewer teeth 16' further allows sections 50 (shown in FIG. 5) of the hemisphere to be removed while maintaining a high quality of cut surface. An example of a acetabular reamer with sections cut away is given in the diagrams of PCT applications Ser. Nos. PCI/IB01/02675 and PCI/IB01/02676 entitled HOLDER FOR A SURGICAL REAMER and SUR- GICAL REAMER, respectively, filed on 21 Dec. 2001, the contents of which are incorporated herein by reference thereto.

The present invention generates a tooth 16' with a wider cutting profile that is therefore easier to overlap with the cut generated by the next tooth at a different latitudinal elevation on the hemisphere. Additionally the tooth 16' cuts a sector of the required hemisphere, matching the required radius exactly. The improved tooth allows a full hemisphere to be cut with fewer teeth than the typical cheese grater-type reamer.

Preferably, the reamer 10' includes a series of cutting teeth 16' arranged uniformly and spaced apart on the cutting shell. These teeth 16' may be arranged in a spiral arrangement on the cutting shell 12'.

Figure 5:
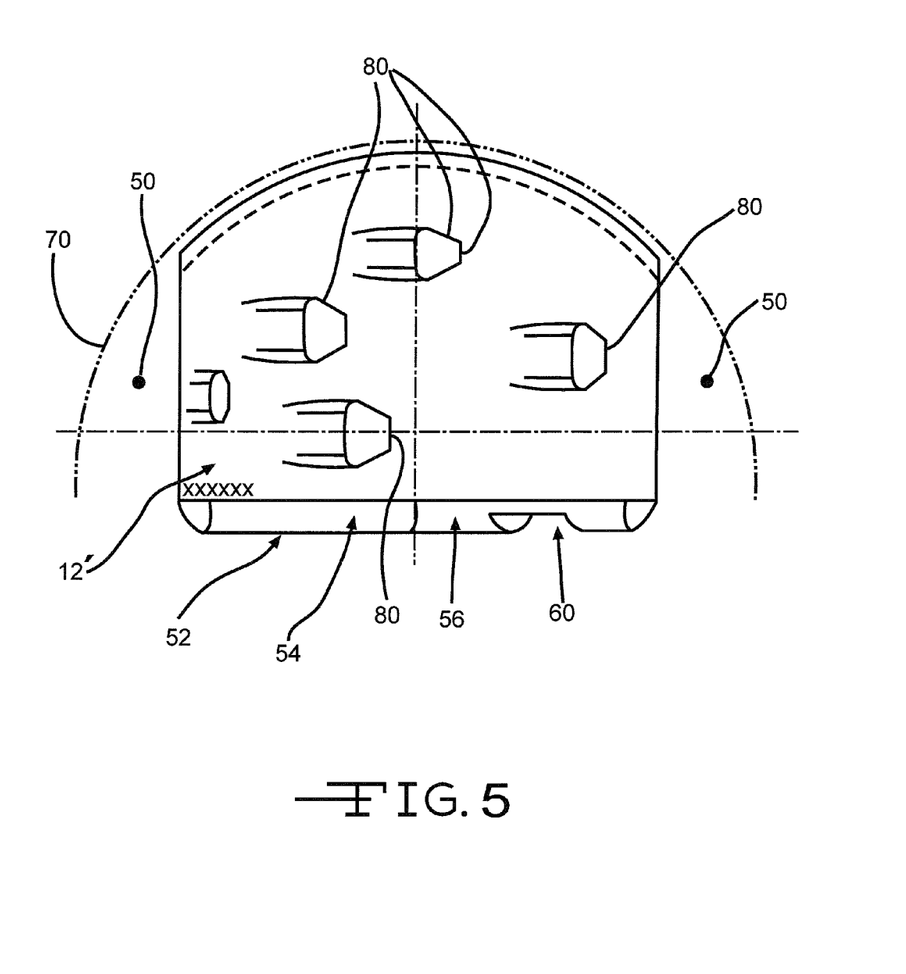
FIG. 5 is a side view of the reamer of the invention.

In an alternate embodiment, best seen in FIG. 5, the cutting shell is a portion of a hemisphere, in this case, in which sections 50 (shown by dashed lines) have been removed in the manufacturing process. In this embodiment, the length of the cutting edges are selected so as to completely cut the shape while being of a number that still ensures good mechanical strength. The longer cutting edges allows the use of less teeth while still cutting a good hemispherical form than permissible with a cutting shell that has a more complete hemispherical shape.

A tool engaging portion 52 is comprised of two intersecting bars 54 and 56, one bar 54 of which optionally having two flats 60 (only one of which is shown) on its outer ends, adjacent their connecting points on the reamer cutting shell 12'.

Figure 6A:
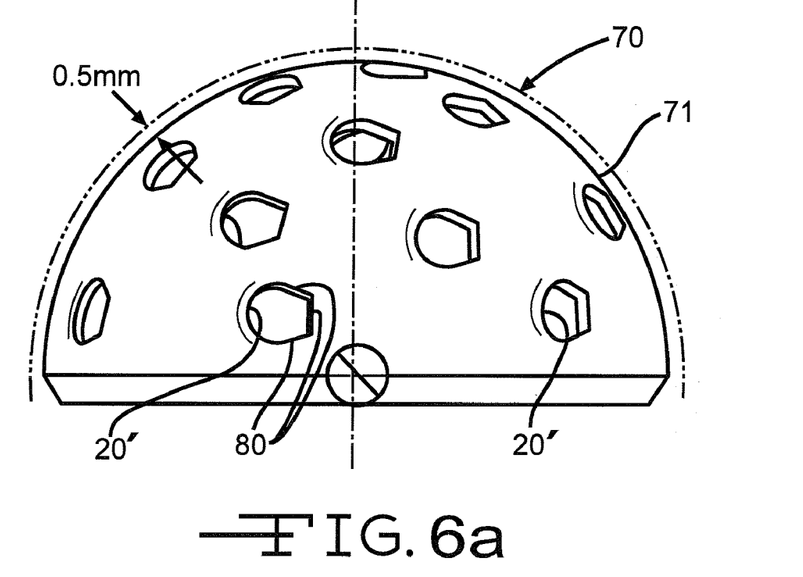
FIG. 6a is a cross sectional side view of the reamer of the invention.
Figure 6B:
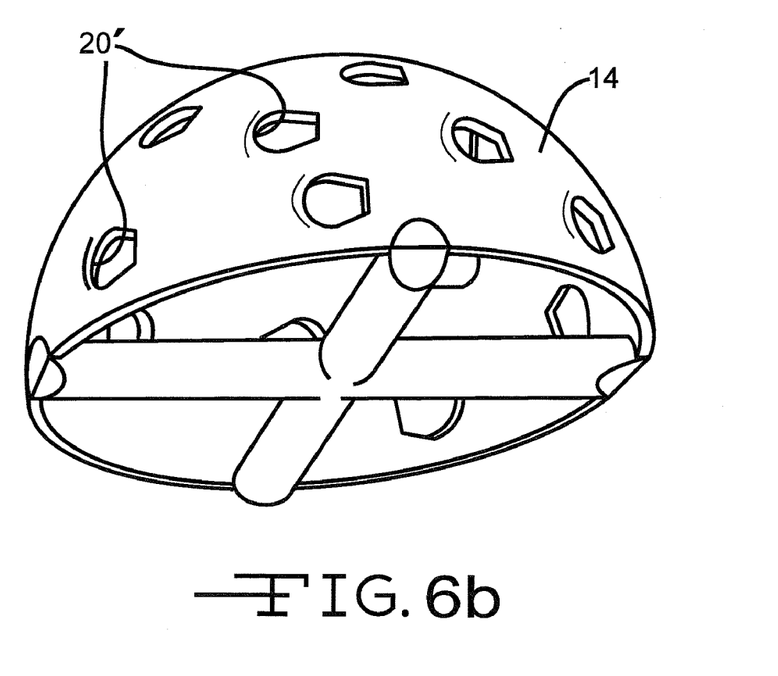
FIG. 6b is a perspective view of the reamer of the invention.

Referring now to FIGS. 6a and 6b, after the cutting edge 20' of the polygonal aperture 18', made up of a curved portion and at least one straight edge 80, is cut via laser in the hemispherical shell 12', a punch (not shown) of corresponding polygonal form (for which the circumferential location of the edge of the punch used to punch up the cutting edge of the reamer is a know and accurately controlled circumferential distance away from a corresponding flat of the punch) is used to punch up the cutting edge, preferably an amount of 0.5 mm, which is half the amount that such teeth are typically punched up. The straight edges 80 of the aperture 18' orient the punch of corresponding polygonal cross section, to ensure that the cutting edge pushed up by the punch is in an optimal orientation with respect to the cutting direction. FIG. 6a shows the cutting profile 70 as compared to the profile 71 of the hemispherical shell 14.

Figure 7:
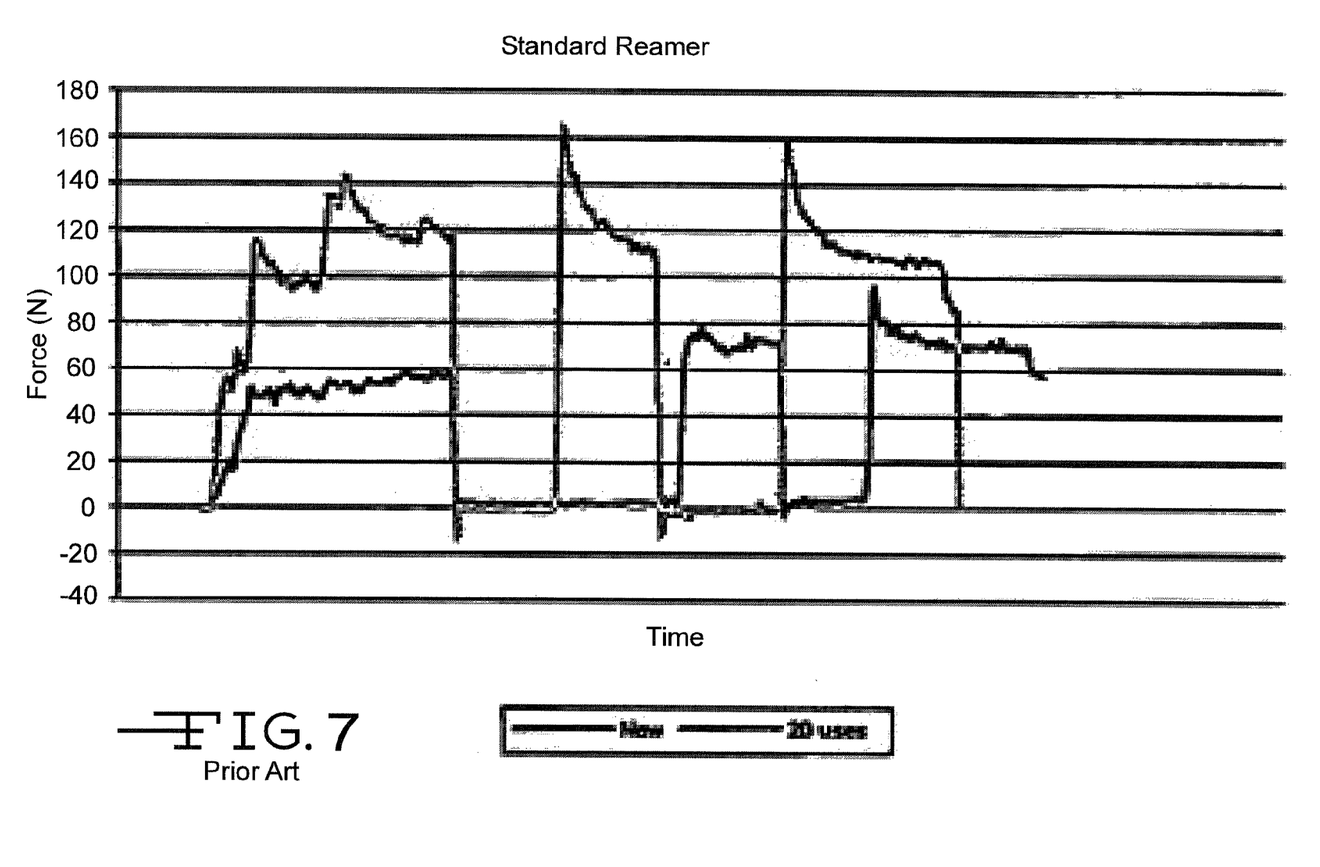
FIG. 7 is a table of the wear characteristics of a prior art reamer.
Figure 8:
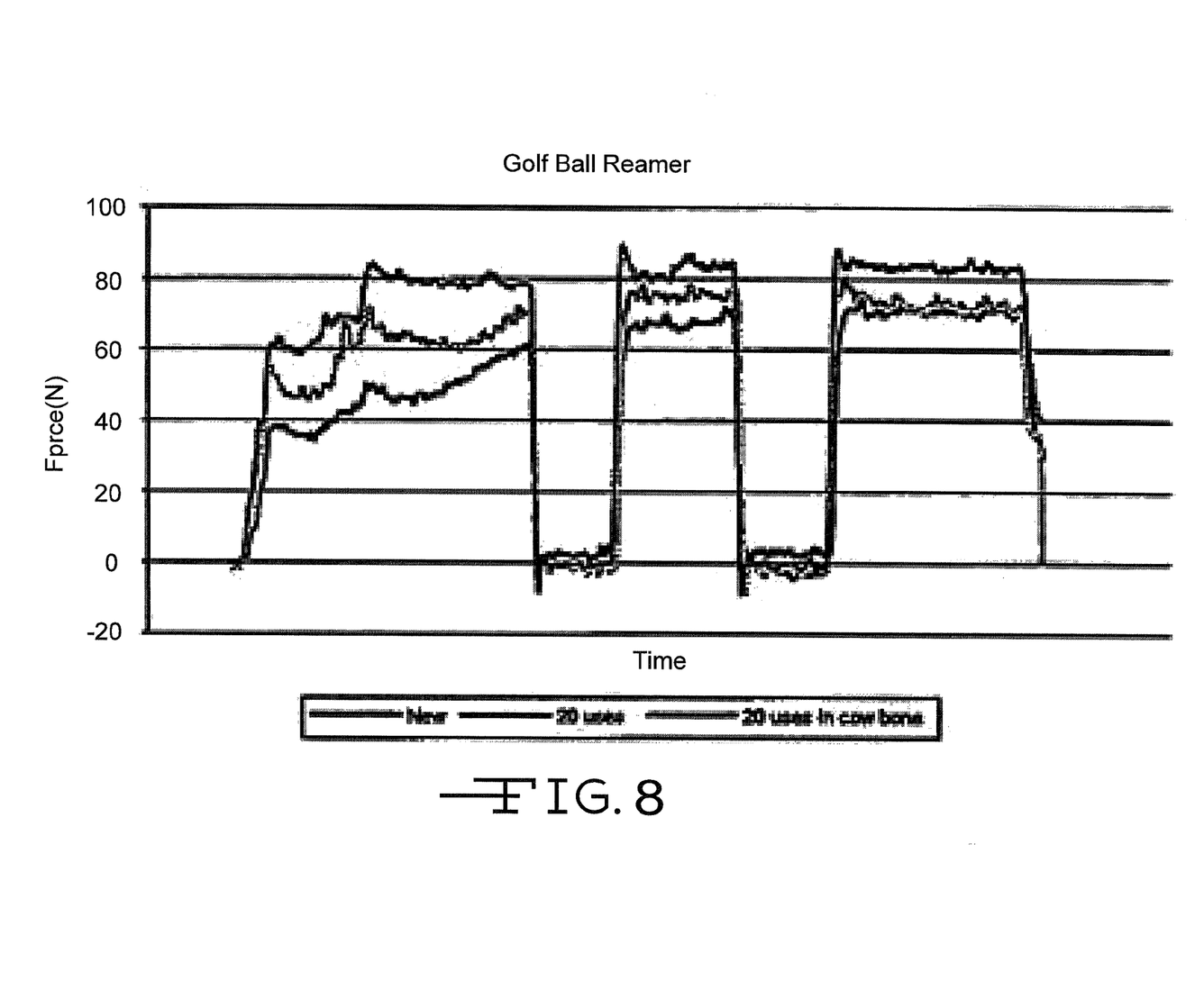
FIG. 8 is a table of the wear characteristics of the reamer of the invention.

Referring now to FIGS. 7 and 8, it is believed that this lesser penetration into the bone, combined with the contour shape of the teeth (in which each tooth cuts a form corresponding to the form of the cavity being cut), reduces stresses, and heat generation, with the result being significantly increased wear life of the reamer. The graph of FIG. 7 is a graph of force vs time for a prior art reamer 10 showing how quickly the cutting forces increase with time. By contract, referring to FIG. 8, the same graph of force vs time for the reamer 10' of the present invention shows that the cutting forces remain relatively constant over as many as 20 uses, about two times less than a cheese-grater-type reamer. Lower cutting forces mean lower heat generation and less dead tissue. Less dead tissue improves the recovery time of the patient.

Figure 9:
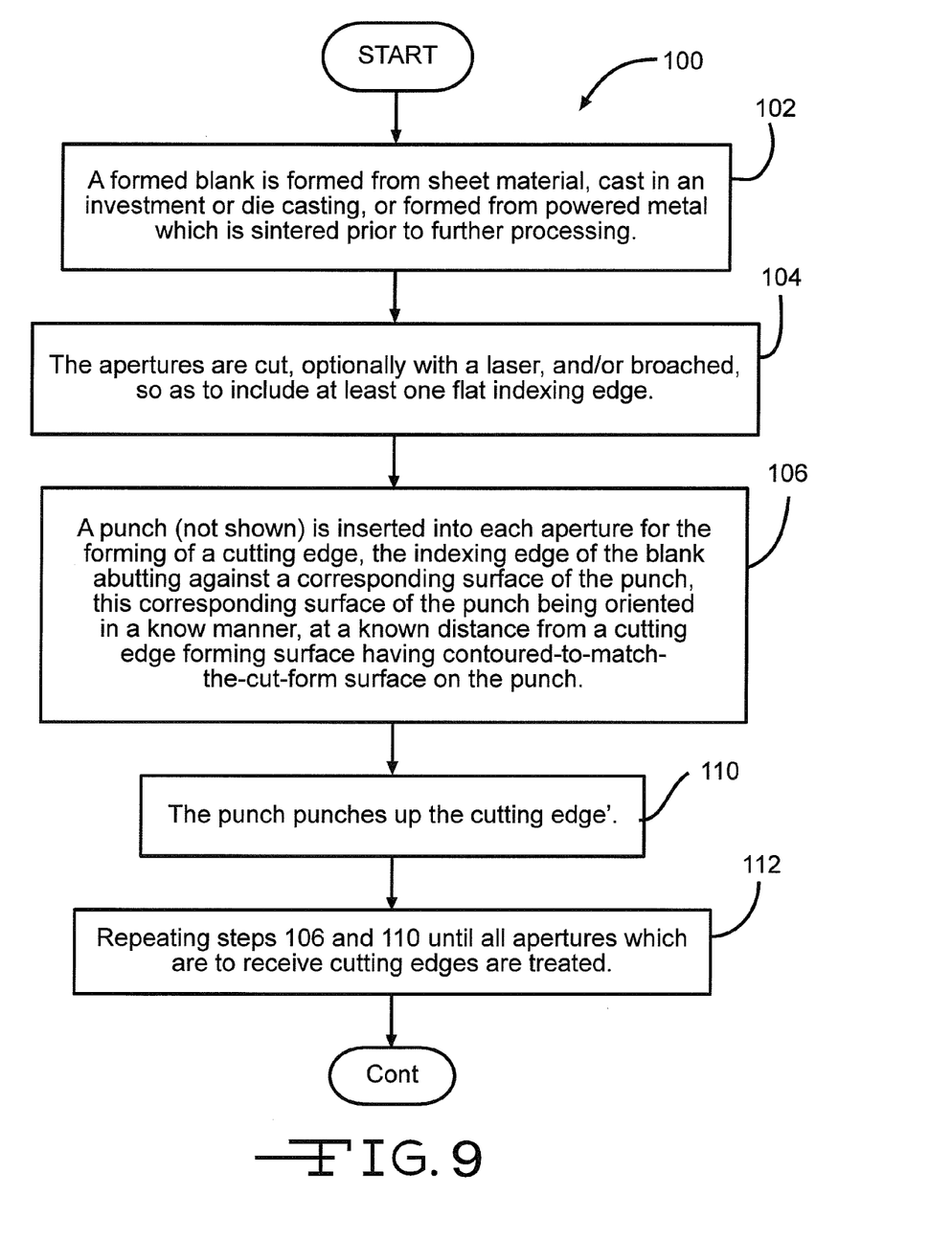
FIG. 9 is a flow chart of the method of manufacturing the invention.

Referring now to FIG. 9, the method 100 of fabrication of the invention includes several steps. In a first step 102, a formed blank is formed from sheet material, cast in an investment or die casting, or formed from powered metal which is sintered prior to further processing. In a second step 104, the apertures 18' are cut, optionally with a laser, and/or broached, so as to include at least one flat indexing edge. In a third step 106, a punch (not shown) is inserted into each aperture for the forming of a cutting edge, the flat indexing edge of the blank abutting against a corresponding surface of the punch, this corresponding surface of the punch being oriented in a known manner, at a known distance from a cutting edge forming surface having contoured-to-match-the-cut-form surface on the punch. In a fourth step 110, via the contoured-to-match-the-cut-form surface on the punch, the punch punches up the cutting edge 20'. In further steps 112, steps 106 and 110 are repeated until all apertures which are to receive cutting edges are treated, after which, the processed blank is sent downstream for the mounting of cross bars 52 and 54, and further final finishing steps.

In an advantage, a reamer is provided which substantially reduces a cutting pressure on each tooth as well as reduces the size of a typical chip generated upon cutting.

In another advantage, because all the teeth each have a matched arc cutting edge of substantial length itself having a cutting profile which substantially matches a profile of a shape to be cut, the number of teeth required to cut the desired shape is reduced.

In another advantage, the apertures on which the cutting edges are formed are non-circular, thus providing an indexing surface permitting the accurate locating of tools which form the cutting edge.

In another advantage, the invention results in improved quality of the cut and orientation of the cutting edge, thereby improving the quality of the cut surface and permitting fewer teeth to be used.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. An acetabular reamer, which comprises:
   a) a cutting shell defining a spherical center and having a shell curvature comprising at least a portion of a first hemisphere extending from an apex to a lower edge, the cutting shell being rotatable about a longitudinal axis;
   b) a plurality of cutting teeth thereon, wherein each cutting tooth comprises two buttress portions extending from the cutting shell and meeting an intermediate cutting edge having a curvature as a line segment of a second hemisphere, wherein the line segment comprises a continuum of cutting edge radii, each radii originating at the spherical center with the second hemisphere being greater than the first hemisphere of the cutting shell and wherein the plurality of cutting teeth are rotatable about the longitudinal axis; and
   an opening directly opposite each cutting tooth in an orientation of intended rotation of the reamer during cutting, wherein the opening comprises a first straight edge directly opposite the cutting edge, the first straight edge having a length extending to opposed ends thereof meeting second and third edge portions of the opening with the second and third edge portions in turn being directly connected to the respective buttress portions of the cutting tooth.

2. The reamer of claim 1 wherein the plurality of cutting teeth are arranged uniformly and spaced apart on the cutting shell.

3. The reamer of claim 1 wherein the plurality of cutting teeth are arranged in a spiral configuration on the cutting shell.

4. The acetabular reamer of claim 1 wherein the second. and third edge portions are straight edges connected to the first straight edge, and wherein opposite ends of the second and third straight edges extend to and meet with the respective buttress portions of the cutting tooth.

5. A reamer, which comprises:
   a) a cutting shell defining a spherical center and having a shell curvature comprising at least a portion of a first hemisphere extending from an apex to a lower edge, the cutting shell being rotatable about a longitudinal axis;
   b) a plurality of cutting teeth extending upwardly from the cutting shell, each cutting tooth comprising two buttress portions extending from the cutting shell and meeting an intermediate cutting edge spaced furthest from the shell, the intermediate cutting edge having a cutting curvature as a line segment of a second hemisphere, wherein the line segment comprises a continuum of cutting edge radii, each radii originating at the spherical center with the second hemisphere being greater than the first hemisphere of the cutting shell and wherein the plurality of cutting teeth are rotatable about the longitudinal axis;
   c) an opening directly opposite each cutting tooth in an orientation of intended rotation of the reamer during cutting, wherein the opening comprises a first straight edge directly opposite the cutting edge, the first straight edge having a length extending to opposed ends thereof meeting second and third straight edge portions of the opening connected to the first straight edge with opposite ends of the second and third straight edge portions in turn being directly connected to the respective buttress portions of the cutting tooth; and
   d) wherein the cutting edges of the plurality of cutting teeth extending upwardly from the cutting shell are in an overlapping arrangement so that rotation of the reamer against bone cuts a shaped cavity into the bone having a relatively smooth contour matching the curvature of the cutting shell.

6. A reamer, which comprises:
   a) a cutting shell having a curvature defined by a plurality of cutting shell radius of the same length extending from a focal point located on a longitudinal axis about which the reamer is rotatable;
   b) a plurality of cutting teeth thereon, wherein each cutting tooth comprises two buttress portions extending from the cutting shell and meeting an intermediate cutting edge spaced furthest from the cutting shell, the cutting edge being continuously defined from one buttress to the other buttress by a continuum of cutting edge radii of the same length with each radii extending from the same focal point as the plurality of cutting shell radii; and
   c) an opening directly opposite each cutting tooth in an orientation of intended rotation of the reamer during cutting, wherein the opening comprises a first straight edge directly opposite the cutting edge, the first straight edge having a length extending to opposed ends thereof meeting second and third edge portions of the opening with the second and third edge portions in turn being directly connected to the respective buttress portions of the cutting tooth.

7. The reamer of claim 6 wherein the second and third edge portions are straight. edges connected to the first straight edge, and wherein opposite ends of the second and third straight. edges extend to and meet with the respective buttress portions of the cutting tooth.

8. The reamer of claim 6 wherein the plurality of cutting teeth are arranged uniformly and spaced apart on the cutting shell.

9. The reamer of claim 6 wherein the plurality of cutting teeth are arranged in a spiral configuration on the cutting shell.

10. The reamer of claim 6 wherein the cutting shell is a hemisphere or portion thereof.

11. An acetabular reamer, which comprises:
    a) a cutting shell having a curvature comprising at least a portion of a first hemisphere defining a spherical center and extending from an apex to a lower edge, the cutting shell being rotatable about a longitudinal axis;
    b) at least one cutting tooth thereon, wherein the cutting tooth comprises two buttress portions extending from the cutting shell to a cutting edge furthest from the cutting shell, the cutting edge having a cutting curvature as a line segment of a second hemisphere, wherein the line segment comprises a continuum of cutting edge radii, each radii originating at the spherical center with the second hemisphere being greater than the first hemisphere of the cutting shell and wherein the cutting tooth is rotatable about the longitudinal axis; and
    c) an opening directly opposite the cutting tooth in an orientation of intended rotation of the reamer during cutting, wherein the opening comprises a first straight edge directly opposite the cutting edge, the first straight edge having a length extending to opposed ends thereof meeting second and third edge portions of the opening with the second and third edge portions in turn being directly connected to the respective buttress portions of the cutting tooth.

* * * * *